United States Patent
Greep (10) Patent No.: US 6,951,559 B1
(45) Date of Patent: *Oct. 4, 2005

(54) UTILIZATION OF A HYBRID MATERIAL IN A SURFACE COATING OF AN ELECTROSURGICAL INSTRUMENT

(75) Inventor: Darcy W. Greep, South Jordan, UT (US)

(73) Assignee: Megadyne Medical Products, Inc., Draper, UT (US)

(*) Notice: Subject to any disclaimer, the term of this patent is extended or adjusted under 35 U.S.C. 154(b) by 66 days.

This patent is subject to a terminal disclaimer.

(21) Appl. No.: 10/177,351

(22) Filed: Jun. 21, 2002

(51) Int. Cl.⁷ .............................................. A61B 18/12
(52) U.S. Cl. ......................................... 606/41; 606/45
(58) Field of Search ................................... 606/41–52

(56) References Cited

U.S. PATENT DOCUMENTS

| | | |
|---|---|---|
| 4,197,217 A | 4/1980 | Gartshore et al. |
| 4,314,559 A | 2/1982 | Allen |
| 4,509,327 A | 4/1985 | Enga |
| 4,754,754 A | 7/1988 | Garito et al. |
| 4,785,807 A | 11/1988 | Blanch |
| 5,030,218 A | 7/1991 | Alexander |
| 5,051,241 A | 9/1991 | Pfefferle |
| 5,197,962 A | 3/1993 | Sansom et al. |
| 5,295,978 A * | 3/1994 | Fan et al. ................ 604/265 |
| 5,417,933 A | 5/1995 | Pfefferle |
| 5,509,899 A | 4/1996 | Fan et al. |
| 5,549,604 A | 8/1996 | Sutcu et al. |
| 5,558,900 A | 9/1996 | Fan et al. |
| 5,589,545 A | 12/1996 | Ramachandran et al. ... 525/184 |
| 5,702,387 A | 12/1997 | Arts et al. |
| 5,713,895 A | 2/1998 | Lontine et al. |
| 5,731,087 A | 3/1998 | Fan et al. |
| 5,800,427 A | 9/1998 | Zamba |
| 5,885,281 A | 3/1999 | Urueta |
| 5,925,039 A | 7/1999 | Landingham |
| 5,925,043 A | 7/1999 | Kumar et al. |
| 5,935,529 A | 8/1999 | Saito et al. |
| 6,106,523 A | 8/2000 | Morris |
| 6,132,427 A | 10/2000 | Jones et al. |
| 6,139,547 A | 10/2000 | Lontine et al. |
| 6,270,831 B2 * | 8/2001 | Kumar et al. ............ 427/2.24 |

(Continued)

OTHER PUBLICATIONS

Mikos, A. G. et al. *"Laminated Three-Dimensional Biodegradable Foams For Use In Tissue Engineering"*, 1993, Biomaterials, vol. 14, No. 5, pp 323-330.

(Continued)

Primary Examiner—Michael Peffley
Assistant Examiner—Aaron Roane
(74) Attorney, Agent, or Firm—Workman Nydegger (57) ABSTRACT

Applying and utilizing a hybrid material in a surface coating to provide or enhance properties, attributes and/or characteristics to the surface, such as at least a portion of an electrosurgical electrode tip. The hybrid material includes a combination of at least one of an organic polymer, an inorganic polymer, or an organic material with at least one of a ceramic or a silicon. The presence of the hybrid material coating layer provides a high temperature stability that withstands the temperatures of electrosurgery and a flexibility to increase the durability of the surface. Other materials may be included in the surface coating, such as a fluoropolymer, a water-soluble polymer, catalytic particles that may be activated or other materials that enhance the properties, characteristics and/or attributes of the coated surface. Optionally, an additional covering layer may be applied over the hybrid material coating layer to enhance the characteristics of the coated surface.

33 Claims, 5 Drawing Sheets

U.S. PATENT DOCUMENTS

| | | | |
|---|---|---|---|
| 6,409,725 B1 * | 6/2002 | Khandkar et al. | 606/45 |
| 6,544,596 B2 | 4/2003 | Clemens et al. | |
| 6,551,267 B1 | 4/2003 | Cohen et al. | |
| 6,558,686 B1 | 5/2003 | Darouiche | |
| 6,558,798 B2 | 5/2003 | Zhong et al. | |
| 6,559,132 B1 | 5/2003 | Holmer | |
| 6,685,704 B2 * | 2/2004 | Greep | 606/41 |
| 2001/0031964 A1 | 10/2001 | Gentelia et al. | |
| 2003/0109864 A1 | 6/2003 | Greep et al. | |
| 2003/0109865 A1 | 6/2003 | Greep et al. | |

OTHER PUBLICATIONS

Ikada, Ph.D., Y. et al. *"Lubricious Polymer Surfaces"*, 1993, Lubricating Polumer Surfaces, pp 41-71.

* cited by examiner

UTILIZATION OF A HYBRID MATERIAL IN A SURFACE COATING OF AN ELECTROSURGICAL INSTRUMENT

BACKGROUND OF THE INVENTION

1. The Field of the Invention

The present invention relates to coated electrosurgical instruments. More specifically, the present invention relates to using a hybrid material in a coating layer of an electrosurgical instrument surface in order to introduce and/or enhance properties, characteristics and/or attributes at the surface.

2. The Relevant Technology

In the area of electrosurgery, medical procedures of cutting tissue and/or cauterizing leaking blood vessels are performed by utilizing radio frequency (RF) electrical energy. The RF energy is produced by a signal generator and is transmitted to a hand-held electrode that is operated by a surgeon. The hand-held electrode delivers an electrical discharge to cellular matter of the patient's body adjacent to the electrode. The discharge causes the cellular matter to heat up in order to cut tissue and/or cauterize blood vessels.

The high temperatures involved in electrosurgery can cause charred matter to form and become affixed to the electrode tip. The buildup of charred matter can reduce the efficiency of the cutting and/or cauterizing processes by creating an insulating barrier that interferes with the transference of RF energy to the targeted area. By way of example, when cauterizing an area to prevent bleeding, the charred matter can inhibit the cauterization, cause the destruction of additional tissue and increase thermal tissue damage. Thus, buildup of the charred matter can slow the surgical procedure, as the surgeon is required to remove the charred matter from the electrode tip.

The application of a fluoropolymer as a coating layer on at least a portion of an electrosurgical electrode tip has proven to be a valuable asset in providing additional properties to the tip, including providing a non-stick surface and a high temperature stability. However, while the anti-adhesion properties of fluoropolymers, such as polytetrafluoroethylene ("PTFE") or Teflon®, as a coating layer on an electrode tip has facilitated electrosurgical cutting and/or cauterizing by reducing the buildup of debris on the electrode tip, it has not completely eliminated such buildup. Accordingly, it would be an improvement in the art to augment or even replace the fluoropolymer coating with other anti-adhesion materials.

BRIEF SUMMARY OF THE INVENTION

The present invention relates to the utilization of a hybrid material in a surface coating. More specifically, the present invention relates to using a hybrid material, which can include a combination of at least one of an organic polymer, an inorganic polymer, or an organic material with at least one of a ceramic or a silicon, in a coating layer of an electrosurgical instrument surface in order to introduce and/or enhance properties, characteristics and/or attributes at the surface.

Implementation of an exemplary embodiment of the present invention takes place in association with a surface, such as at least a portion of the surface of an electrosurgical electrode tip that may be used to cut tissue and/or cauterize blood vessels of a patient during a surgical operation. At least a portion of the conductive electrode tip is coated with a hybrid material coating layer. The hybrid material can include a combination of at least one of an organic material and an inorganic material, and provides the coated surface with desirable properties, such as a high temperature stability, flexibility, and a low temperature application condition so that the coating layer may be applied by a spray or dip process.

The hybrid material is advantageously compatible with other materials. As such, the hybrid material may be mixed with, reacted with, applied to, or otherwise bonded to a supplementary material prior to having the hybrid material and supplementary material applied as a surface coating layer to enhance properties and/or provide additional properties at the surface. For example, the hybrid material may be mixed with, reacted with, applied to, or otherwise bonded to particles of a fluoropolymer and applied as a surface coating to the electrode tip to increase the nonstick character of the coated tip. Similarly, a water-soluble polymer may be mixed with, reacted with, applied to, or otherwise bonded to the hybrid material to provide an attraction of water at the coated surface. Other supplementary materials include an active catalyst, such as a noble metal, that may provide a release property of accumulated buildup to a coated surface, and other materials that may be mixed with, reacted with, applied to, or otherwise bonded to the hybrid material to provide additional properties, characteristics and/or attributes that are desired at the coated surface.

Alternatively or additionally, the hybrid material coating layer may be at least partially coated with a covering layer, which may include, for example, a water-soluble polymer, such as polyethylene oxide, a fluoropolymer, such as polytetrafluoroethylene, or catalytic particles, such as particles of a noble metal, to introduce and/or augment properties, characteristics and/or attributes at the surface.

While the methods and processes of the present invention have proven to be particularly useful in the area of electrosurgery, those skilled in the art can appreciate that the methods and processes of the present invention can be used on a variety of different kinds of surfaces and in a variety of different areas of manufacture to yield a coated surface that has desired properties for performing a particular task.

Additional features and advantages of the present invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The present invention relates to the utilization of a hybrid material in a surface coating. More specifically, the present invention relates to using a hybrid material in a coating layer of at least a portion of an electrosurgical instrument surface in order to introduce and/or enhance properties, characteristics and/or attributes at the surface.

In the disclosure and in the claims the term "hybrid material" shall refer to a material that includes a combination of at least one of an organic material and an inorganic material. For instance, the "hybrid material" can include, but not limited to, a combination of one or more organic polymers, inorganic polymers, or organic materials with at least one of a ceramic or a silicon. As such, the hybrid material is a hybrid of organic and inorganic materials, which are characterized by primary (covalent) chemical bonds joining their organic and inorganic components. An acid or base may be used to generate a reaction to produce the hybrid material. The term "hybrid material" is to be interpreted broadly and includes, for example, an ORMOSIL™ (an organically modified silicate), an ORMOCER™ (an organically modified ceramic), a CERAMER® (a ceramic polymer), and other organic-inorganic materials.

In one embodiment, the hybrid material used in the present invention is a durable, heat resistant, pliable material that is created by combining silica with a small amount of one or more organic compounds. By way of example, the incorporation of about ten percent of an organic polymer into a ceramic via a sol-gel solution method results in a rubbery hybrid material that may be used to coat a surface. The rubbery behavior is possible due to the formation of chemical bonds between the oxide and polymer chains. The coiling and uncoiling of the polymer chains under stress results in the rubbery behavior. One example of using a hybrid material to coat a surface is discussed in U.S. Pat. No. 6,096,437, entitled "Ceramer Coating Compositions" that issued on Aug. 1, 2000 to Soucek, et al., which is incorporated herein by reference.

In the disclosure, reference is made to the use of a "supplementary material." In the disclosure and in the claims the term "supplementary material" shall refer to any material that may be mixed with, react with, applied to, or otherwise bonded to a hybrid material, whether before or after applying the hybrid materials to a surface. Examples of supplementary materials include a fluoropolymer, a water-soluble polymer, a catalyst, such as a noble metal, and other materials that are capable of withstanding high temperatures, such as the high temperatures required to perform electrosurgery, and may be associated with a hybrid material in a surface coating.

In the disclosure and in the claims, the term "fluoropolymer" shall refer to a material that includes polymers that contain fluorocarbons or fluorinated hydrocarbons. By way of example, the term "Teflon®" represents a family of various fluoropolymers.

Also, in the disclosure and in the claims the term "binder" or "binder material" shall refer to a material that may be used in association with a catalyst in a coating layer. Examples of binder materials include a ceramic, a silicon, a metal, a polymer, a sol gel deposition, and other materials that are capable of withstanding the high temperatures of electrosurgery.

The following disclosure of the present invention is grouped into three subheadings, namely "Exemplary Operating Environment," "Application of a Hybrid Material Coating Layer" and "Application of a Covering Layer." The utilization of the subheadings is for convenience of the reader only and is not to be construed as limiting in any sense.

Exemplary Operating Environment

Figure 1:
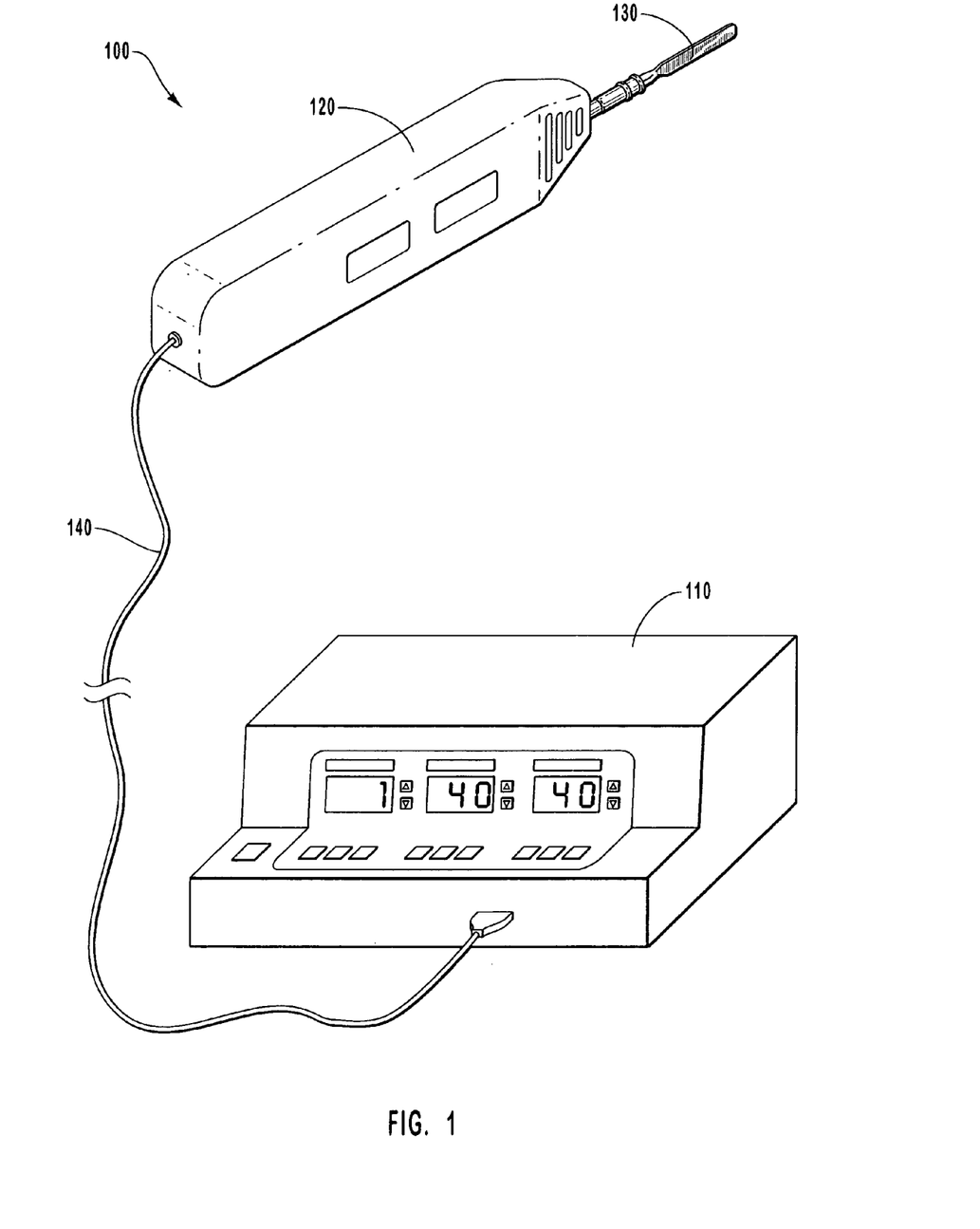
FIG. 1 illustrates an exemplary system that provides a suitable operating environment for use of the present invention.
Figure 2A:
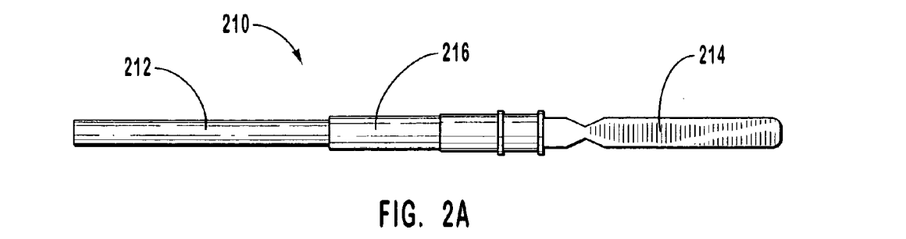
FIG. 2A illustrates an exemplary electrosurgical electrode tip for use in the suitable operating environment of FIG. 1 to cut tissue and cauterize blood vessels in general surgery.
Figure 2B:
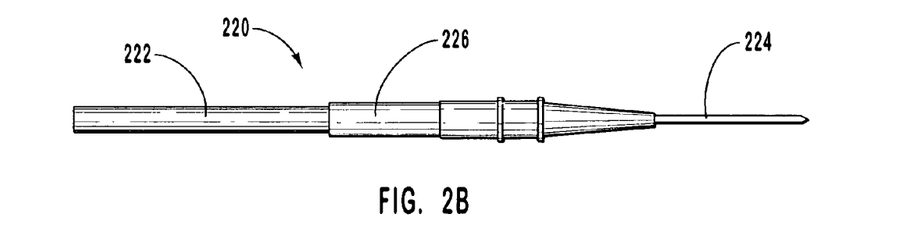
FIG. 2B illustrates an exemplary electrosurgical electrode tip for use in the suitable operating environment of FIG. 1 to cut tissue and cauterize blood vessels in particularly dense areas.
Figure 2C:
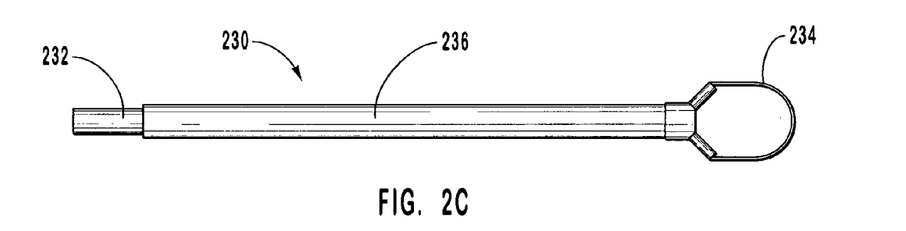
FIG. 2C illustrates an exemplary electrosurgical electrode tip for use in the suitable operating environment of FIG. 1 to remove large sections of tissue.
Figure 2D:
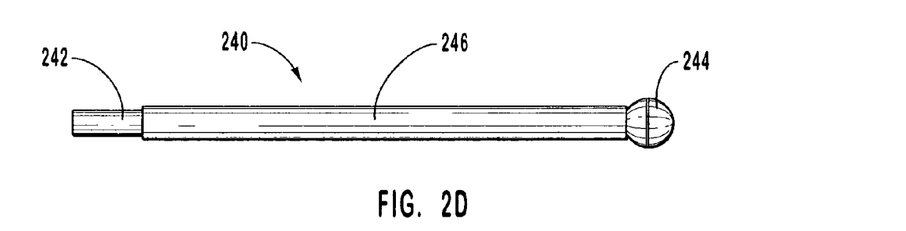
FIG. 2D illustrates an exemplary electrosurgical electrode tip for use in the suitable operating environment of FIG. 1 to cauterize leaking blood vessels and to seal open structures.
Figure 2E:
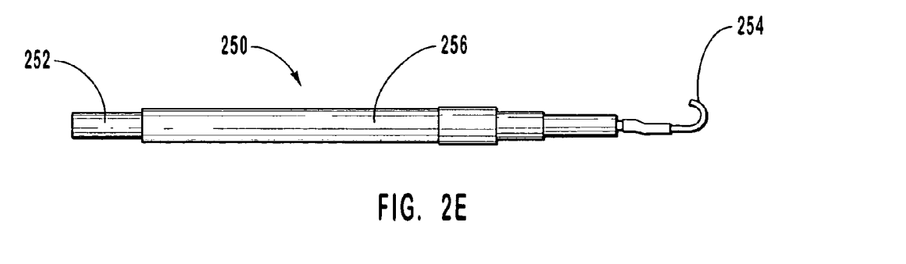
FIG. 2E illustrates an exemplary electrosurgical electrode tip for use in the suitable operating environment of FIG. 1 to isolate tissue and to independently cut or cauterize.

FIGS. 1–2E and the corresponding discussion are intended to provide a brief, general description of one operating environment in which one embodiment of the invention may be implemented. Although not required, the invention will be described in the general context of providing specific properties, attributes and/or characteristics to a surface of an electrosurgical instrument. Those skilled in the art, however, will appreciate that embodiments of the present invention may be practiced in association with a variety of different surfaces in order to provide desirable properties, attributes and/or characteristics at the surfaces.

Referring to FIG. 1, an exemplary environment is illustrated that provides one operating environment for use of the present invention. In FIG. 1, electrosurgical instrument 100 is illustrated, which includes a signal generator 110, a hand-held electrode 120, and an electrode tip 130. A surgeon typically may use electrosurgical instrument 100 during surgical procedures to cut tissue and/or cauterize blood vessels of a patient's body.

In electrosurgery, radio frequency (RF) electrical energy is produced by a signal generator, such as signal generator 110, and is introduced to a patient's body by a hand-<held electrode, such as electrode 120, which is electrically coupled to signal generator 110 and includes tip 130. The RF electrical energy powers electrode 120 and is transmitted from signal generator 110 to electrode 120 via cord 140. An electrical discharge is delivered from tip 130 to the patient in order to cause the heating of cellular matter of the patient that is in extremely close contact to tip 130. The heating takes place at an appropriately high temperature to allow electrode 120 to be used to perform electrosurgery. A grounding electrode (not shown) may be employed to carry away any excess charge that dissipated into surrounding tissue of the patient's body.

During electrosurgery, electrode 120 may be used to independently or concurrently cut and cauterize. A constant sinusoidal signal supplied by signal generator 110 and transmitted to electrode 120 allows tip 130 to cut through tissue of the patient's body. Alternatively, a damped wave signal supplied by signal generator 110 and transmitted to electrode 120 allows tip 130 to cauterize leaking blood vessels. A combination of the constant sinusoidal signal and the damped wave signal can be supplied by signal generator 110 to electrode 120 for allowing tip 130 to concurrently cut and cauterize, thereby minimizing tissue trauma and blood loss during the surgical procedure.

FIGS. 2A–2E illustrate an exemplary assortment of interchangeable tips for use with electrode 120 to facilitate the acts of cutting tissue and/or cauterizing blood vessels. Each of the interchangeable tips has a first end that can be coupled to the hand-held electrode, an insulator, and a second end that applies the discharge to the patient's body. The configuration of the second end allows for a great versatility of the acts of cutting and/or cauterizing in a variety of different surgical procedures.

By way of example, FIG. 2A illustrates tip 210, which is an electrode tip that may be used in general surgery for cutting tissue and/or for cauterizing blood vessels. End 212 is coupled to the hand-held electrode to allow the RF electrical energy, generated from the signal generator and transmitted to the hand-held electrode, to be transmitted through tip 210. A discharge is delivered to the patient's body from end 214, which is in a blade-like configuration. In this illustrative configuration, end 214 has two parallel sides that are flat to allow end 214 to function in a similar manner as a traditional scalpel; however, end 214 can have various other configurations as known to those skilled in the art, including but not limited to sharpened sides or partially sharpened sides. In the illustrated configuration, rather than employing a mechanical action for cutting through tissue, the electrical discharge allows end 214 to slide through the tissue as the tissue is being superheated to an appropriate temperature to perform the electrosurgical procedure. A coating 216 surrounds at least a portion of tip 210 and acts as an insulator.

Similarly, FIG. 2B illustrates tip 220, which is an electrode tip that may be used for cutting tissue and cauterizing leaking blood vessels in particularly dense areas of a patient's body, such as those experienced in cerebral operations. End 222 is coupled to the hand-held electrode to allow the RF electrical energy, generated from the signal generator and transmitted to the hand-held electrode, to be transmitted through tip 220. A discharge is delivered to the patient's body from end 224, which is in a needle-like configuration that comes to a point to allow for very accurate surgical procedures in dense areas of the patient's body. A coating 226 surrounds at least a portion of tip 220 and acts as an insulator. Through the use of tip 220, delicate cerebral tissues can be accurately removed with virtually no damage to any surrounding membranes and with minimal bleeding and/or swelling resulting from the procedure.

FIG. 2C illustrates tip 230, which is an electrode tip that may be used for the removal of large sections of tissue, as in, for example, prostate and tumor excision. End 232 is coupled to the hand-held electrode to allow the RF electrical energy to be transmitted through tip 230. A discharge is delivered to the patient's body from end 234, which is in a loop-like configuration. A coating 236 surrounds at least a portion of tip 230 and acts as an insulator.

FIG. 2D illustrates tip 240, which is an electrode tip that may be used to specifically cauterize leaking blood vessels and to seal open structures. End 242 is coupled to the hand-held electrode to allow the RF electrical energy to be transmitted through tip 240. A discharge is delivered to the patient's body from end 244, which is in a spherical configuration. A coating 246 surrounds at least a portion of tip 240 and acts as an insulator.

FIG. 2E illustrates tip 250, which is an electrode tip that may facilitate a surgeon in reducing extraneous tissue damage by allowing individual tissues or blood vessels to be isolated and independently cut and/or cauterized. End 252 is coupled to the hand-held electrode to allow the RF electrical energy from the signal generator to be transmitted through tip 250. A discharge is delivered to the patient's body from end 254, which is in a hook-like configuration. A coating 256 surrounds at least a portion of tip 250 and acts as an insulator.

Ends 214, 224, 234, 244 and 254 are examples of surfaces upon which a coating may be applied to provide one or more desirable attributes and/or properties at the surface. When the surface is at least a portion of an electrode tip, an example of a desired property includes a high temperature stability to withstand the temperatures of electrosurgery and a flexibility to increase the durability of the electrode tip.

Application of a Hybrid Material Coating Layer

A coating of a surface may include a hybrid material to introduce and/or enhance properties, characteristics and/or attributes at the surface. The hybrid material may introduce and/or enhance hardness, strength (e.g., compressive strength, shear strength, etc.), and/or flexibility of a surface. Furthermore, a hybrid material may be applied at a low temperature, such as 150° C., as compared to other coating materials, such as a fluoropolymer that requires approximately 300–400° C. for application onto a surface.

In one embodiment, the hybrid material used in the present invention to coat a surface is a durable, heat resistant, pliable material that is created by combining silica with a small amount of organic compounds. As provided above, an example of using a hybrid material to coat a surface is discussed in U.S. Pat. No. 6,096,437, entitled "Ceramer Coating Compositions" that issued on Aug. 1, 2000 to Soucek, et al.

Figure 3:
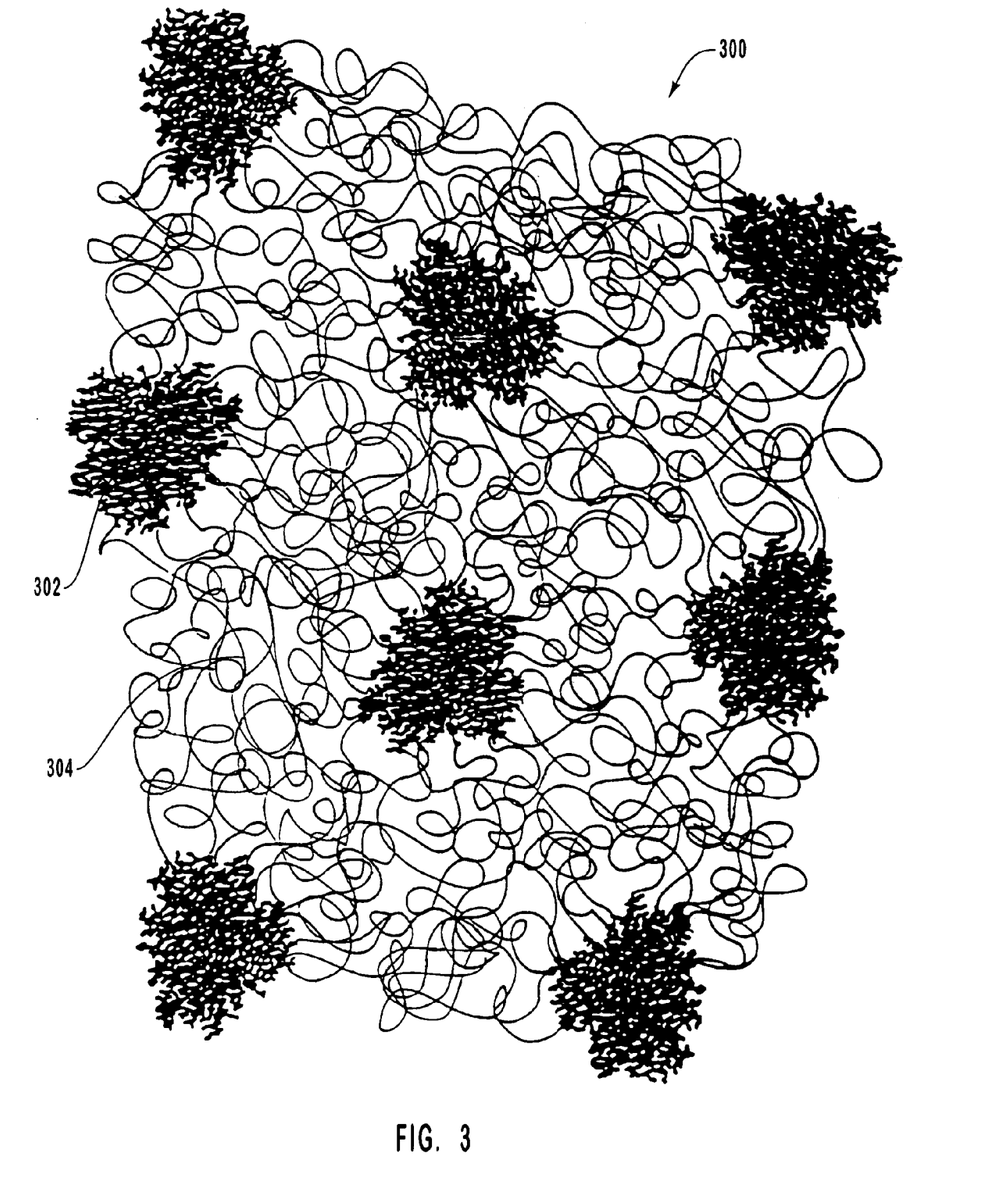
FIG. 3 illustrates an exemplary structure of a hybrid material having organic domains and inorganic domains.

With reference to FIG. 3, an illustration is provided of an exemplary structure of a hybrid material, illustrated as hybrid material 300. In FIG. 3, hybrid material 300 includes a plurality of different domains, illustrated as domains 302 and domains 304. Domains 302 represent components of silicon or ceramic and are denser than domains 304 that represent components of an organic material, such as but not limited to an organic polymer or an inorganic material, such as but not limited to an inorganic polymer. In another configuration, domains 302 and domains 304 have the same or substantially the same density. In one embodiment, hybrid material 300 includes a rubber-like characteristic, much like a silicone, and a high temperature stability.

As identified above, hybrid material 300 can be used to coat a surface to introduce and/or enhance properties, characteristics and/or attributes at the surface. When the surface that is to be coated by the hybrid material is an electrosurgical electrode tip, the hybrid material coating layer provides a high temperature stability that withstands the temperatures of electrosurgery and a flexibility to increase the durability of the surface.

Figure 4A:
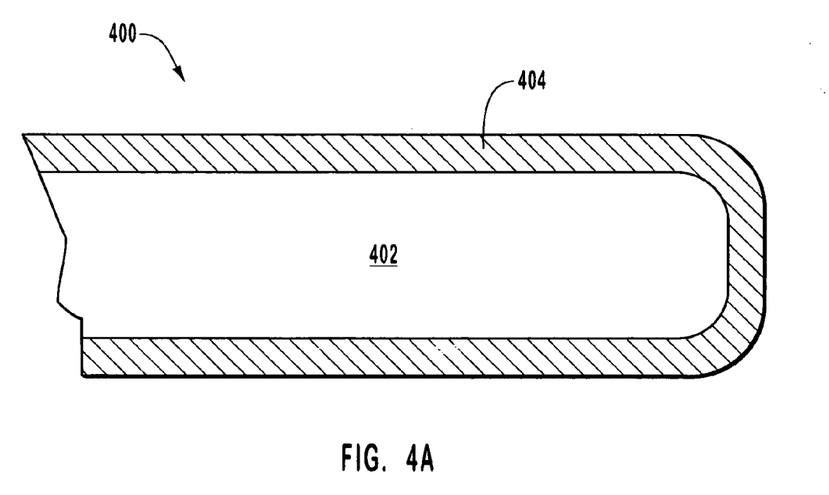
FIG. 4A illustrates an exemplary cross-sectional view of an electrosurgical electrode tip that has a hybrid material coating layer applied thereon, the coating layer including a hybrid material and optionally one or more supplementary materials.

With reference to FIG. 4A, an exemplary cross-sectional view of an electrosurgical electrode tip is illustrated as electrode tip 400, which includes a substrate 402 and a hybrid material coating layer 404 applied thereon. In one embodiment, substrate 402 includes a metal, such as surgical stainless steel. In other embodiments, substrate 402 can be fabricated from any metal, alloy, composite material, combinations thereof, or other material(s) that is capable of conducting RF energy. The substrate 402 can have one or more smooth portions, one or more rough portions, or combinations thereof.

Prior to applying hybrid material coating layer 404 onto electrode tip 400, the surface of substrate 402 may be prepared, for example, by being heat cleaned in order to remove any oils or contaminants and may be roughened to provide a footing for the coating layer 404. Additionally, the surface of substrate 402 may be roughened before applying hybrid material coating layer 404.

Once the surface of substrate 402 is prepared, the hybrid material coating layer 404 may be applied to at least a portion of the substrate 402. The low temperature application of the hybrid material allows the hybrid material coating layer 404 to be applied to the substrate 402 through the utilization of a spray process, a dip process, or another low temperature application process.

While an embodiment of the present invention relates to the hybrid material coating layer 404 including only one or more hybrid materials, other embodiments embrace the inclusion of other supplementary materials in the hybrid material coating layer 404 to introduce and/or enhance properties, characteristics and/or attributes at the electrode tip 400. This is the case, since a hybrid material is typically compatible with other materials. For example, the hybrid material and one or more supplementary materials may be mixed prior to having the mixture applied as a surface coating layer.

Examples of supplementary materials that may be mixed with, reacted with, applied to, or otherwise bonded to a hybrid material include a water-soluble polymer, a fluoropolymer, catalytic particles, and/or other materials that are capable of withstanding the high temperatures of electrosurgery and provide or enhance properties, attributes and/or characteristics at the surface. Foe example, a water-soluble polymer may be used as a supplementary material in a coating layer of an electrosurgical electrode tip to provided an attraction of water at the tip.

Examples of a water-soluble polymer include, but are not limited to, polyethylene oxide ("PEO"), polyethylene glycol ("PEG"), polyethylene oxide-poly(dimethylsiloxane) copylmer ("PEO-PDMS"), polyvinyl pyrrolidone, polyvinyl alcohol ("PVA"), polypropylene oxide ("PPO"), polylactone, polycaprolactone and other caprolactone copolymers, starch, methylcellulose, ethylcellulose, hydroxyethylcellulose, hydroxypropyl-methylcellulose, ethyl-hydroxyethylcellulose, ethyl-methylcellulose, hydroxyethyl-methylcellulose, carboxymethylcellulose and salts thereof, carboxymethylhdroxyethylcellulose salts, other cellulosic derivatives, poly-4-vinyl-n-butylpyridinium bromide, polyvinylmethyl ether, vinylmethyl ether-maleic anhydride copolymer, gelatin, polyacrylic acid, ammonium polyacrylate, ethylene maleic anhydride copolymer and other maleic anhydrides, polyalkylene oxalate, ionene (ionic amine) polymers, chitin—poly(N-acetyl-D-glucosamine) and derivatives, hyaluronic acid and salts thereof, other polysaccharides, chondritic sulfate, agarose, water soluble nylone, ethylene-vinyl acetate copolymers, other copolymers of ethylene oxide, other water-soluble polymers, combinations of one or more of the above, and the like.

In one configuration, the water-soluble polymer, for example, may be mixed directly into the hybrid material prior to applying the mixture, such as by dipping, spraying, or another low temperature application process, as a hybrid material coating layer 404 on the substrate 402 of the electrode tip. In other configurations, the water-soluble polymer can be reacted with, applied to, or otherwise bonded to the hybrid material before applying the hybrid material and water-soluble polymer to surface or after the hybrid material has been applied to the surface.

The presence of the water-soluble polymer in the hybrid material coating layer 404 typically causes an attraction of water to the surface of the tip that may assist in cooling the tip by evaporation during use of the electrode, thereby protecting and prolonging the service life of the coated tip. The water-soluble polymer may also act as a radical scavenger or inhibitor to reduce damage that may occur to the coated electrode tip during a process of gamma sterilization, thereby improving the properties and service life of the coated tip. The water-soluble polymer may further act as a carrier of antibiotic factors, healing factors, anti-adhesion factors, anti-tumor factors, tumor necrosis factors, combinations of one or more of the same, and the like, which are specifically included in the coating layer as desired, and by design, for deposition in and on tissues of a patent's body where electrosurgical procedures are performed.

Other examples of supplementary materials that may be mixed with, reacted with, applied to, or otherwise bonded to a hybrid material prior to applying the hybrid material coating layer 404 include particles of a fluoropolymer or a catalyst. The particles of a fluoropolymer may be mixed into, reacted with, applied to, or otherwise bonded to the hybrid material prior to applying the hybrid material and particles of the fluoropolymer as a hybrid material coating layer 404 onto the substrate 402. In one embodiment, once the surface of substrate 402 is prepared through the processes of heat cleaning and roughening, a suspension of fluoropolymer particles and an etching agent, such as but not limited to, an acid, is mixed with, reacted with, applied to, or otherwise bonded to the hybrid material. The material may then be spray-coated onto the substrate 402 so as to uniformly apply hybrid material coating layer 404 onto at least a portion of substrate 402. The etching agent improves the bond of the coating layer to the substrate 402. Alternatively, the hybrid material coating layer 404 may be applied onto the substrate 402 through the use of a dip process or another application process. The presence of the fluoropolymer enhances a nonstick character at the coated tip, which reduces the amount of charred blood and/or tissue, known as eschar, that accumulates or builds-up on the tip during an electrosurgical procedure. The nonstick character increases the efficiency of the electrode tip in cutting tissue and/or cauterizing blood vessels and facilitates the removal from the electrode tip of eschar that may have accumulated on the tip.

When the supplementary material added to the hybrid material includes catalytic particles, such as micro or nano-sized particles of a noble metal, the coating layer is applied such that at least a portion of the catalytic particles (not shown) are located at the exposed surface of the hybrid material coating layer 404. As such, an application of the hybrid material coating layer 404 may include applying a thickness of the hybrid material coating layer 404 onto substrate 402 that is less than or equal to the diameter of the micro or nano-sized catalytic particles. As will be further explained below, once applied to the electrosurgical electrode tip, the catalytic particles may be activated by an energy source to cause a release of eschar from the electrosurgical electrode tip that may have accumulated or built-up on the tip during an electrosurgical procedure. The ability of an electrosurgical instrument to release accumulated eschar therefrom increases the efficiency of the instrument in cutting tissue and/or cauterizing blood vessels.

Application of a Covering Layer

At times, it is advantageous to apply a covering layer over at least a portion of a hybrid material coating layer to introduce or augment properties, characteristics or attributes at the surface.

Figure 4B:
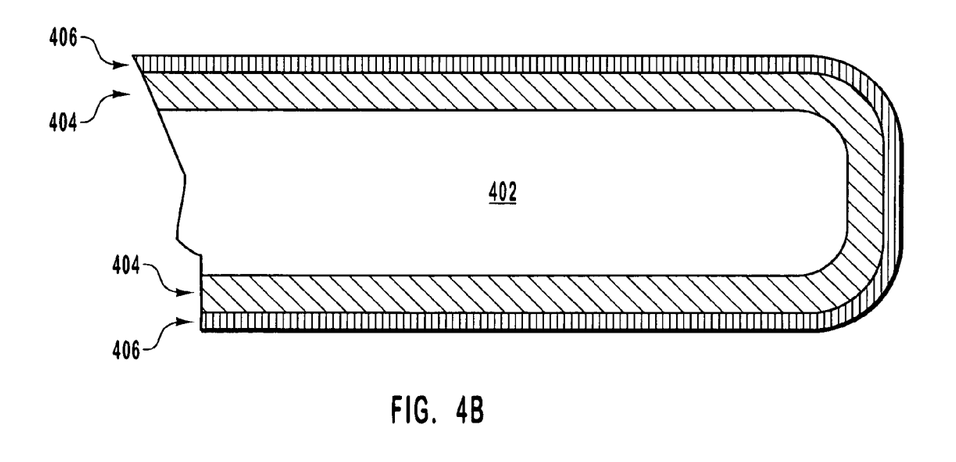
FIG. 4B illustrates an exemplary cross-sectional view of the electrode tip of FIG. 4A that further includes a covering layer applied thereon, the covering layer including one or more supplementary materials.

With reference to FIG. 4B, an exemplary cross-sectional view of the electrode tip of FIG. 4A is provided that further includes a covering layer 406 applied thereon. Covering layer 406 may be applied to at least a portion of hybrid material coating layer 404, which is applied to at least a portion of substrate 402. When the covering layer 406 includes a water-soluble polymer, the covering layer typically causes an attraction of water and may provide or further enhance the various properties to the tip that were discussed above in association with the inclusion of a water-soluble polymer in a hybrid material coating layer.

Alternatively, the covering layer 406 may include a suspension of a fluoropolymer and an etching agent that may be spray-coated onto at least a portion of the hybrid material coating layer 404. As explained above, the presence of a fluoropolymer typically provides or enhances a non-stick property to the surface. Thus, a covering layer 406 that includes a fluoropolymer may provide or further enhance a non-stick property at the electrode tip.

Figure 4C:
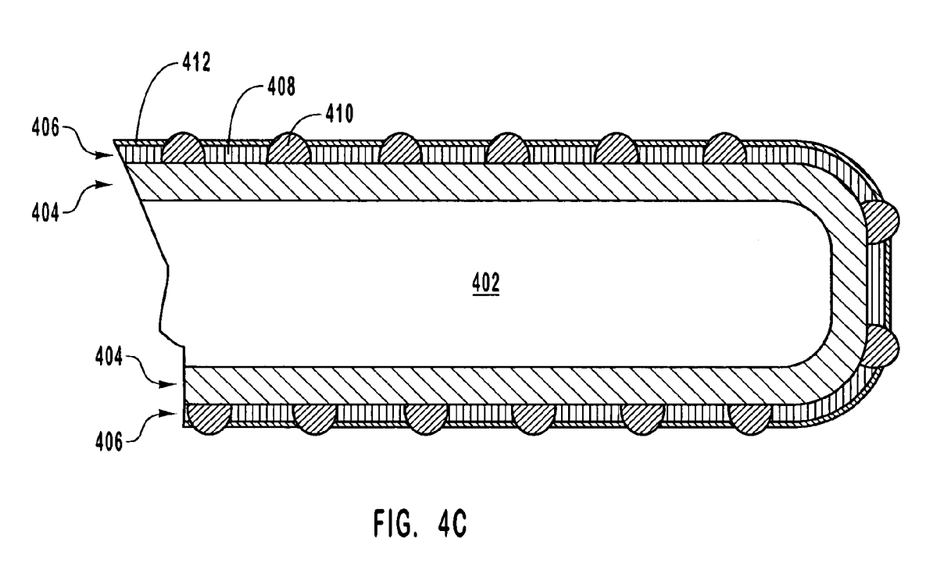
FIG. 4C illustrates an exemplary cross-sectional view of the electrode tip of FIG. 4A that includes a covering layer applied thereon, wherein the covering layer includes catalytic particles, a binder material, and optionally a water-soluble polymer.

Additionally or alternatively, a covering layer may include catalytic particles, such as micro or nano-sized particles of a noble metal, which may be activated to enable a release of eschar that has accumulated on the surface. Thus, FIG. 4C provides an exemplary cross-sectional view of an electrosurgical electrode tip that includes a substrate 402 and a hybrid material coating layer 404 that may receive a catalytic coating layer on at least a portion thereof. In one embodiment, the catalytic particles are embedded directly on at least a portion of the hybrid material coating layer. By way of example, catalytic particles may be embedded through the use of a sputter technique. The catalytic particles bond to the hybrid material coating layer and at least a portion of the catalytic particles are exposed in order to react with accumulated eschar when activated, as will be further explained below. In other embodiments, catalytic particles are mixed with a binder material, such as a ceramic, a silicon, a metal, a polymer, a sol gel deposition, a hybrid material, prior to being applied to the hybrid material coating layer. In one such embodiment, the catalytic particles are mixed with a suspension of fluoropolymer particles and an etching agent. The mixture is then spray-coated as a covering layer onto at least a portion of the hybrid material coating layer.

In FIG. 4C, covering layer 406 is illustrated as including catalytic particles 410 and a binder material 408. In one embodiment, the thickness of binder material 408 is less than or equal to the diameter of the catalytic particles to allow at least a portion of the catalytic particles to be exposed or located on the outer surface of the covering layer 406. As such, the catalytic particles are able to be in direct contact with eschar that may have accumulated on the electrode tip 400 and may be activated by an energy source to provide a release character of the accumulated eschar, as will be explained below. While the catalytic particles illustrated in FIG. 4C are uniformly spaced and shaped, embodiments of the present invention allow for variations in the size, shape and spacing of the catalytic particles. Furthermore, one or more of the catalytic particles may not be in contact with the hybrid material coating layer.

Optionally, an additional coating layer 412 may be applied onto at least a portion of the covering layer 406 so as to allow at least a portion of the catalytic particles to remain exposed to be able to contact accumulated eschar. The water-soluble coating layer 412 may provide or augment properties, attributes and/or characteristics to the tip, such as causing an attraction of water to the surface even when the surface is otherwise hydrophobic, such as when the surface includes an anti-adhesion fluoropolymer. As provided above, the attraction of water at an electrosurgical electrode tip may provide various useful purposes in the area of electrosurgery; such as assisting in cooling the tip by evaporation during use of the electrode and/or acting as a lubricant for an enhanced release character of the coated tip. The water-soluble coating layer may also introduce and/or enhance properties discussed above in relation to including a water-soluble polymer into the hybrid material coating layer. The properties include, for example, providing a low shear, sacrificial layer, acting as a radical scavenger or inhibitor and acting as a carrier of one or more factors as discussed above.

The catalytic particles of a covering layer may be activated to advance a release of accumulated eschar from the surface of an electrosurgical electrode tip. An energy source, such as a heat source, a light source, a microwave source, or other electromagnetic radiation source, may be coupled to or cooperate with the electrosurgical instrument to activate the catalytic particles. The active catalytic particles break bonds between the eschar and the surface of the electrode tip, allowing the eschar to release from the tip.

In one embodiment, and with reference back to FIG. 1, the energy source that activates the catalytic particles on an electrode tip is signal generator 110, which provides RF electrical energy to electrode 120 and the corresponding electrode tip 130. The RF electrical energy powers the electrode 120 so that an electrical discharge is delivered from tip 130 that heats cellular matter of the patient in extremely close contact to the tip 130 and activates the catalytic particles of the tip 130. The heating takes place at an appropriately high temperature to allow electrode 120 to be used to perform electrosurgery and to activate the catalytic particles. By way of example, the process of activating catalytic particles may take place at temperatures greater than 300° C. and the electrosurgical instrument may generate temperatures over 800° C.

Alternative embodiments embrace a variety of other types of energy sources that are capable of generating the energy to activate the catalytic particles. For example, a light source or microwave source may be coupled to the electrosurgical electrode to provide the activation energy. Alternatively, an electrically resistive coating that heats up in response to the buildup of eschar may be applied on the tip to provide the required energy. Furthermore, a button (not shown) on the electrode may be selected by a user to cause the energy source to temporarily activate the catalytic particles in order to release accumulated eschar from the tip. In still another configuration, an external energy source can direct electromagnetic energy toward the tip to activate the catalytic particles. Illustrative devices capable of activating the catalytic particles are described in co-pending U.S. patent Ser. No. 14458.43 entitled "Utilization Of An Active Catalyst In A Surface Coating Of An Electrosurgical Instrument," the disclosure of which is incorporated herein by this reference.

When the catalytic particles are activated, the active particles interact with the accumulated eschar constituents. The active catalytic particles react with the carbon or nitrogen based materials in the eschar that may have accumulated on the tip during an electrosurgical procedure. This reaction reduces the chemical adsorption and/or bonding between the accumulated eschar and the electrode tip, thereby enhancing a release of the eschar from the tip.

Thus, as discussed herein, the embodiments of the present invention embrace the application and utilization of a hybrid material on a surface. The hybrid material includes a combination of an organic material, polymer or organic polymer and a ceramic or silicon. At least a portion of the surface, such as an electrosurgical electrode tip, is coated with the hybrid material and optionally other materials, such as supplementary materials to provide and/or enhance properties, characteristics and/or attributes to the surface. While the methods and processes of the present invention have proven to be particularly useful in the area of electrosurgery, those skilled in the art can appreciate that the methods and processes of the present invention can be used on a variety of different kinds of surfaces and in a variety of different areas of manufacture to yield a coated surface that has desired properties for performing a particular task.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. An electrosurgical instrument comprising: an electrode including an appropriately sized and configured conductive tip for performing an electrosurgical procedure; and a coating on at least a portion of the tip, wherein the coating includes a hybrid material comprised of at least one of a polymer or organic material and at least one of a ceramic or silicon and a fluoropolymer.

2. An electrosurgical instrument as recited in claim 1, wherein the coating further includes an etching agent.

3. An electrosurgical instrument as recited in claim 1, wherein the coating further includes one or more catalytic particles.

4. An electrosurgical instrument as recited in claim 3, further comprising an energy source communicating with the tip to activate the catalytic particles, wherein the activated catalytic particles interact with eschar, which accumulated on the tip during an electrosurgical procedure, to release the eschar from the tip.

5. An electrosurgical instrument as recited in claim 4, wherein the energy source includes at least one of:
    a heat source;
    a light source;
    a microwave source; or
    an electromagnetic radiation source.

6. An electrosurgical instrument as recited in claim 1, wherein the coating further comprises a water-soluble polymer.

7. An electrosurgical instrument as recited in claim 6, wherein the water-soluble polymer comprises at least one of:
    (i) polyethylene oxide;
    (ii) polyethylene glycol; or
    (iii) a copolymer of ethylene oxide.

8. An electrosurgical instrument as recited in claim 6, wherein the water-soluble polymer is a radical scavenger that reduces damage to a binder material during a process of gamma sterilization.

9. An electrosurgical instrument as recited in claim 6, wherein the water-soluble polymer is a carrier that deposits a factor on a contact area of a patient's body during the electrosurgical procedure.

10. An electrosurgical instrument as recited in claim 9, wherein the factor includes at least one of:
    (i) an antibiotic factor;
    (ii) a healing factor;
    (iii) an anti-adhesion factor;
    (iv) an anti-tumor factor; or
    (v) a tumor necrosis factor.

11. An electrosurgical instrument as recited in claim 6, wherein the water-soluble polymer provides a low shear, sacrificial layer to the tip.

12. A tip that may be used in association with an electrosurgical electrode for performing an electrosurgical procedure, the tip comprising: a substrate, and a coating applied to at least a portion of the substrate, wherein the coating includes a hybrid material comprised of at least one of a polymer or organic material and at least one of a ceramic or silicon and a fluoropolymer.

13. A tip as recited in claim 12, wherein the substrate is conductive.

14. A tip as recited in claim 13, wherein the substrate includes surgical stainless steel.

15. A tip as recited in claim 13, wherein the substrate includes roughened metal.

16. A tip as recited in claim 12, wherein the coating further includes an etching agent.

17. A tip as recited in claim 12, wherein the coating further includes a water-soluble polymer.

18. A tip as recited in claim 17, wherein the water-soluble polymer includes at least one of:
    (i) polyethylene oxide;
    (ii) polyethylene glycol; or
    (iii) a copolymer of ethylene oxide.

19. A tip as recited in claim 17, wherein the water-soluble polymer is a radical scavenger that reduces damage to a binder material during a process of gamma sterilization.

20. A tip as recited in claim 17, wherein the water-soluble polymer provides a low shear, sacrificial layer.

21. A tip as recited in claim 17, wherein the water-soluble polymer is a carrier that deposits a factor on a patient during an electrosurgical procedure.

22. A tip as recited in claim 21, wherein the factor comprises at least one of:
    (i) an antibiotic factor;
    (ii) a healing factor;
    (iii) an anti-adhesion factor;
    (iv) an anti-tumor factor; or
    (v) a tumor necrosis factor.

23. A tip as recited in claim 12, wherein the coating further includes one or more catalytic particles that may be activated to interact with eschar that accumulated on the tip during an electrosurgical procedure, and wherein the interaction breaks one or more bonds between the eschar and the tip to allow a release of the eschar from the tip.

24. A tip as recited in claim 23, wherein the coating includes a first layer and a second layer, wherein the second layer is on at least a portion of the first layer, and wherein the first layer includes the hybrid material and the second layer includes the catalytic particles and a binder material that comprises at least one of:
(i) a fluoropolymer;
(ii) a ceramic;
(iii) a silicon;
(iv) a metal; or
(v) a sol gel deposition.

25. A tip as recited in claim 24, wherein the coating further includes a third layer, located on top of at least a portion of the binder material, that includes a water-soluble polymer.

26. A method for coating a tip of an electrosurgical electrode, the method comprising the acts of:
providing a tip of an electrosurgical electrode; and applying a coating to the tip, wherein the coating includes a hybrid material comprised of at least one of a polymer or organic material and at least one of a ceramic or silicon and a fluoropolymer.

27. A method as recited in claim 26, wherein the tip is conductive, and wherein the act of applying a coating includes using at least one of:
(i) a dip process;
(ii) a spray process; or
(iii) a low temperature application process.

28. A method as recited in claim 26, further comprising the act of mixing the hybrid material with a supplementary material prior to performing the act of applying the coating, and wherein the coating further includes the supplementary material.

29. A method as recited in claim 28, wherein the supplementary material includes at least one of:
(i) a water-soluble polymer; or
(ii) a catalytic particle.

30. A method as recited in claim 29, wherein the act of mixing the hybrid material with the supplementary material further includes mixing the hybrid material with an etching agent, and wherein the coating further includes the etching agent.

31. A method as recited in claim 26, further comprising the act of applying a second coating onto at least a portion of the coating, wherein the second coating includes at least one of:
(i) a fluoropolymer;
(ii) a water-soluble polymer; or
(iii) a catalytic particle.

32. A method as recited in claim 31, wherein the second coating includes at least one of:
(i) polyethylene oxide;
(ii) polyethylene glycol; or
(iii) a copolymer of ethylene oxide.

33. A method as recited in claim 32, wherein the second coating includes a carrier that deposits a factor on a patient's body during an electrosurgical procedure.

* * * * *

UNITED STATES PATENT AND TRADEMARK OFFICE
CERTIFICATE OF CORRECTION

PATENT NO. : 6,951,559 B1
DATED : October 4, 2005
INVENTOR(S) : Darcy W. Greep

It is certified that error appears in the above-identified patent and that said Letters Patent is hereby corrected as shown below:

Column 3,
Line 47, after "but" insert -- is --.

Column 4,
Line 63, change "hand-<held" to -- hand-held --.

Column 7,
Line 48, change "Foe" to -- For --.
Line 62, change "carboxymethylhdroxyethylcellulose" to
-- carboxymethylhydroxyethylcellulose --.

Signed and Sealed this

Seventh Day of March, 2006

JON W. DUDAS
*Director of the United States Patent and Trademark Office*